(12) United States Patent
Suzuki et al.

(10) Patent No.: US 6,911,006 B2
(45) Date of Patent: Jun. 28, 2005

(54) PAIN INFERRING DEVICE AND PAIN INFERRING METHOD

(75) Inventors: Takashi Suzuki, Aichi (JP); Shuichi Takeuchi, Aichi (JP); Masato Nishikawa, Aichi (JP); Takashi Shinzato, Aichi (JP); Masahiko Miyata, Aichi (JP)

(73) Assignee: Kabushiki Kaisha Tokai Rika Denki Seisakusho, Aichi (JP)

( * ) Notice: Subject to any disclaimer, the term of this patent is extended or adjusted under 35 U.S.C. 154(b) by 453 days.

(21) Appl. No.: 10/110,877

(22) PCT Filed: Apr. 24, 2001

(86) PCT No.: PCT/JP01/03511

§ 371 (c)(1),
(2), (4) Date: Apr. 16, 2002

(87) PCT Pub. No.: WO01/80744

PCT Pub. Date: Nov. 1, 2001

(65) Prior Publication Data

US 2003/0028083 A1 Feb. 6, 2003

(30) Foreign Application Priority Data

Apr. 26, 2000 (JP) .................................... 2000-125273

(51) Int. Cl.⁷ ................................................. A61B 5/00
(52) U.S. Cl. ...................................................... 600/300
(58) Field of Search ................................. 600/300, 301, 600/587, 592, 595–597; 482/79, 34; 128/920; 400/489; 364/508

(56) References Cited

U.S. PATENT DOCUMENTS 5,813,406 A * 9/1998 Kramer et al. .............. 600/595
6,352,516 B1 * 3/2002 Pozos et al. ................ 600/587

* cited by examiner

*Primary Examiner*—Mary Beth Jones
*Assistant Examiner*—Michael Astorino
(74) *Attorney, Agent, or Firm*—Crompton, Seager & Tufte, LLC

(57) ABSTRACT

A pain inferring device for designing a shape giving a subject as little pain as possible when the subject touches the shape. The pain inferring device includes an input unit, an output unit, a main control unit, a learning storage unit, and a neural network. The neural network learns the relationship between the input value of shape data and the output value of the data on the degree of pain when a subject touches a shape. By the learning, an input/output function (namely, the coefficient of coupling of neurons in layers) representing the relationship between the input and output values is defined and stored in the learning storage unit. When the shape data is inputted through the input unit, the neural network infers the degree of pain by using the function stored in the learning storage unit.

4 Claims, 3 Drawing Sheets

● : Inferred Value
○ : Organoleptic Value

Input Layer    Intermediate Layer    Output Layer

● : Organoleptic Value
○ : Inferred Value

PAIN INFERRING DEVICE AND PAIN INFERRING METHOD

TECHNICAL FIELD

The present invention relates to a pain inferring device, more specifically to a pain inferring device for inferring a pain felt by a person when he or she touches a certain shape.

BACKGROUND OF THE INVENTION

BACKGROUND ART

Taking a switch for example, operating portion thereof is formed to have an uneven surface so as to prevent slipping of operators' fingers during operation. However, operators are likely to feel pain depending on the shape of the uneven surface or on the manner of operating the switch.

Evaluation of the degree of pain in operators has conventionally been practiced by preparing, at the stage of designing an operating portion, those having various types of uneven surface profiles and allowing test subjects to operate the operating portions thus prepared. An optimum shape is then selected based on evaluation of the degree of pain or on measurement to prepare an operating portion giving minimized pain to operators. However, in order to obtain subjective evaluation of degrees of pain by test subjects, there are prepared a number of operating portions, at the stage of designing, so that it takes much time and labor. Thus, it is difficult to easily set out at the stage of designing an operating portion giving as little pain as possible.

BRIEF SUMMARY OF THE INVENTION

DISCLOSURE OF THE INVENTION

It is an object of the present invention to provide a pain inferring device and a pain inferring method capable of designing easily a shape giving minimized pain.

According to one aspect of the present invention, there is provided a pain inferring device. The pain inferring device includes input means, learning means and function storage means. The input means inputs shape data for specifying a shape. The learning means learns the relationship between the shape data as an input and a degree of pain, as an output, felt by a person when he or she touches the shape corresponding to the shape data to produce an input-output function indicative of the relationship between the input and the output. The function storage means stores the input-output function. As soon as the shape data are inputted through the input means, the learning means infers the degree of pain based on the input-output function stored in the function storage means.

According to another aspect of the present invention, there is provided a pain inferring method. The pain inferring method includes the steps of learning a relationship between shape data as an input and a degree of pain, as an output, felt by a person when he or she touches the shape corresponding to the shape data; producing an input-output function indicative of the relationship between the input and the output; and inferring based on an input of new shape data a degree of pain according to the input-output function.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE PREFERRED EMBODIMENTS

A pain inferring device 10 according to a first embodiment of the present invention will be described below referring to FIGS. 1 to 4.

Figure 1:
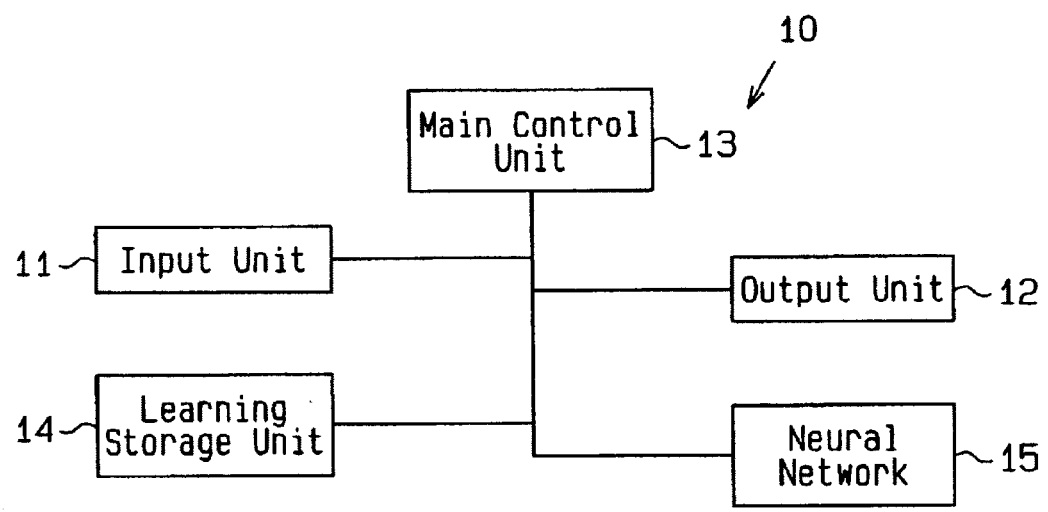
FIG. 1 is a schematic block diagram of a pain inferring device according to one embodiment of the present invention.

As shown in FIG. 1, the pain inferring device 10 is provided with an input unit 11, an output unit 12, a main control unit 13, a learning storage unit 14 and a neural network 15. The main control unit 13 is connected to the input unit 11, the output unit 12, the learning storage unit 14 and the neural network 15. The input unit 11 consists essentially of a keyboard and the like and is used by operators for inputting numerical data including shape data etc. The main control unit 13 includes a central processing unit (CPU), which performs data processing and control of the input unit 11, the output unit 12, the learning storage unit 14 and the neural network 15. The output unit 12 includes a printer and/or a display unit, which outputs data (inferred value) indicative of the degree of pain under control by the main control unit 13.

The neural network 15 functions as learning means and is preferably a hierarchical neural network having an input layer, an intermediate layer and an output layer, each layer including a multiplicity of neurons. The coefficients of coupling between neurons of the input layer and those of the intermediate layer and between neurons of the intermediate layer and that of the output layer are learned preferably in accordance with the known back-propagation algorithm. Here, the back-propagation algorithm may be replaced with any other learning algorithms, so long as its accuracy is permissible. Learning by the neural network 15 will be described later.

The learning storage unit 14, which is preferably a non-volatile semiconductor memory, stores information including the number of layers in the neural network 15, the number of synapses connecting the neurons of the respective layers and coefficients of coupling between the synapses. The information stored in the learning storage unit 14 is handled as an input-output function governing the relationship between the input values and the output value.

Figure 3:
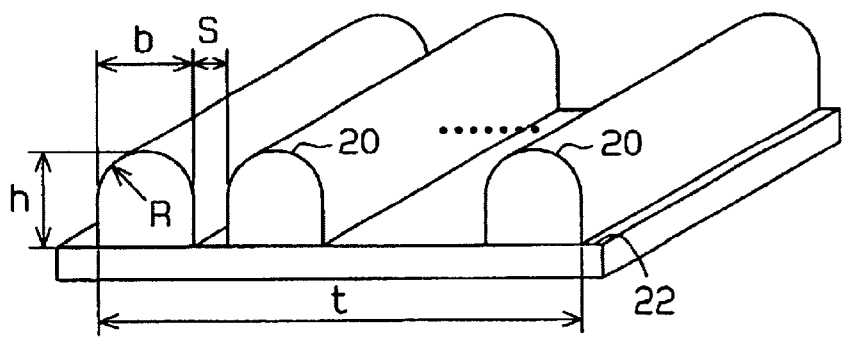
FIG. 3 is a schematic diagram of a test piece having a surface profile similar to that of a switch knob.

The pain inferring device 10 is used, for example, for designing a switch knob (not shown) having a surface profile similar to that of a test piece 22 as shown in FIG. 3. The test piece 22 has on the surface thereof a plurality of ribs 20 arranged parallel to one another.

(Shape Data Setting)

Shape data (hereinafter referred to as shape variables) of the ribs 20 include the height h, the rib-to-rib pitch S, the radius of curvature R at the crest of the rib 20 and the width b of the rib 20. The shape variables are set based on the case where the ribs 20 are formed on a test piece 22 having a length t (30 mm, in this embodiment). Data of nine types of test pieces having ribs 20 with different shape variables are shown in Table 1.

TABLE 1

| Test piece no. | 1-1 | 1-2 | 1-3 | 1-4 | 1-5 | 1-6 | 1-7 | 1-8 | 1-9 |
|---|---|---|---|---|---|---|---|---|---|
| H | 0.5 | 0.5 | 0.5 | 1.0 | 1.0 | 1.0 | 1.5 | 1.5 | 1.5 |
| B | 1.0 | 1.5 | 2.0 | 1.0 | 1.5 | 2.0 | 1.0 | 1.5 | 2.0 |
| R | 0.0 | 0.3 | 0.5 | 0.3 | 0.5 | 0.0 | 0.5 | 0.0 | 0.3 |
| S | 0.5 | 1.0 | 1.5 | 1.5 | 0.5 | 1.0 | 1.0 | 1.5 | 0.5 |

(unit: mm)

(Pain Evaluating Test)

There were provided test pieces 22 based on the nine types of data shown in Table 1, and a pain evaluating test (organoleptic test) was performed using five adult males as test subjects.

Evaluation of pain is performed by calculating the absolute evaluation point using the known Scheffe's paired comparison method (variation of the Haga's method). According to the paired comparison method, each test subject places his or her fingers on a pair of test pieces fixed parallel to each other, and in this state the test pieces are drawn back horizontally from the test subject. The test subject evaluates degrees of pain felt by himself or herself at that moment according to the 7-point rating method (rating in the range of 0±3, by an increment or decrement of 0.5 point) (see "Degree of pain before normalization" in Table 2).

Mean values of these evaluation points for the test pieces are calculated and normalized, respectively. Here, normalization of the mean values is performed as follows:

First, the maximum theoretical value A of the absolute evaluation point is determined according to the following equation (1):

$$A = \alpha \times (\text{Number of samples evaluated} - 1)/\text{Number of samples evaluated} \quad (1)$$

wherein α represents the maximum value of the relative evaluation point. Here, the minimum theoretical value is also determined. Approximate values 1 and 0 are set referring to the maximum theoretical value A and the minimum theoretical value of the absolute evaluation point obtained according to the above equation (1) to perform normalization based on the approximate values 1 and 0.

It should be noted here that, in this test, nine test pieces were used as samples to be evaluated, so that the maximum theoretical value and the minimum theoretical value were calculated to be 2.67 and −2.67 according to the above equation (1), and the approximate values of the maximum value and the minimum value were set at 2.5 and −2.5, respectively, to perform normalization based on these values. Degrees of pain before and after normalization are shown below in Table 2.

TABLE 2

| Test piece no. | 1-1 | 1-2 | 1-3 | 1-4 | 1-5 | 1-6 | 1-7 | 1-8 | 1-9 |
|---|---|---|---|---|---|---|---|---|---|
| Degree of pain before normalization | −1.42 | −0.04 | 0.53 | 1.11 | −0.11 | −0.80 | 1.69 | −0.07 | −0.89 |
| Degree of pain after normalization | 0.22 | 0.49 | 0.61 | 0.72 | 0.48 | 0.34 | 0.84 | 0.49 | 0.32 |

The evaluation point xijl of the assay test piece (one test piece of the two) in comparison with the reference test piece (the other test piece of the two) is assumed according to the following equation (2)

$$xijl = (\alpha i - \alpha j) + gij + eijl \quad (2)$$

In the above equation, i: assay test piece no.;

j: reference test piece no.;

αi: absolute evaluation point of i;

αj : absolute evaluation point of j;

gij: effect to be exhibited by the combination of reference test piece and assay test piece;

l: test subject no.; and eijl: error of test subject

The effect gij to be exhibited by the combination of the reference test piece and the assay test piece is a psychological afterimage effect of evaluation of the previous test piece on the evaluation of the subsequent test piece. Thus, absolute evaluation point αi of each test piece is calculated according to the equation (2).

(Learning by Pain Inferring Device 10)

Figure 2:
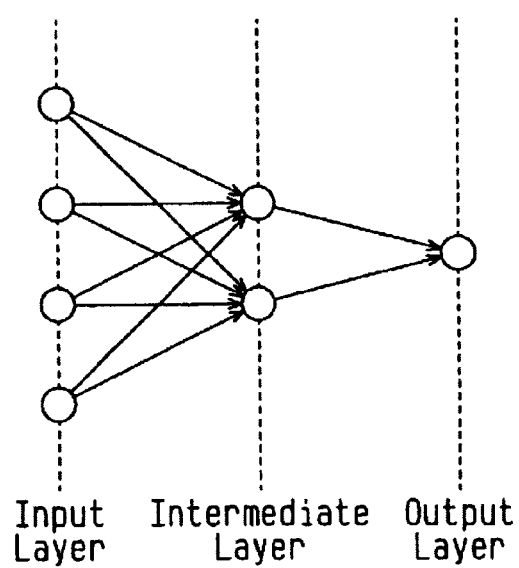
FIG. 2 is a schematic diagram of a neural network of the pain inferring device of FIG. 1.

The shape variables as input values and the absolute evaluation point αi as an output value are inputted through the input unit 11 of the pain inferring device 10 to allow the neural network 15 to learn the relationship between the input and the output. The neural network 15, which is of 4-input and 1-output system, includes an input layer, an intermediate layer and an output layer, as shown in FIG. 2, and learns according to the back-propagation algorithm. The intermediate layer has two elements (neurons). Before inputting to the input unit 11, the input values and the output value are normalized such that they have a maximum value of 0.95 and a minimum value of 0.05. The learning by the neural network 15 is terminated when the error of the output value reduces to a tolerable level of 0.01 or less. The input-output function governing the learned relationship between the input and the output is stored in the learning storage unit 14. It should be noted here that, referring to the degree of pain, the greater the numerical value, the greater the degree of pain, whereas the smaller the numerical value, the smaller the degree of pain. If shape variables are input to the pain inferring device 10 after completion of learning, the device 10 can infer the degree of pain to be given by the shape corresponding to the shape variables.

(Inferred Pain Verification Test)

The degree of pain inferred, after completion of learning, by the pain inferring device 10 (inferred value) was compared with degrees of pain reported by a plurality of (in this embodiment, five adult males) test subjects as the result of an organoleptic test (organoleptic values).

In the verification test, there were prepared seven test pieces each having a shape according to shape variables, which are different from those used in the pain evaluating test. Each test piece was subjected to organoleptic test, whereas the shape variables were input to the pain inferring device 10 to determine the degree of pain. In the pain inferring device 10, as soon as the shape variables are input thereto, the neural network 15 supplies the degree of pain in accordance with the input-output function stored in the learning storage unit 14 to the main control unit 13. In the organoleptic test, degrees of pain were determined according to the equation (2) to calculate a mean value like in the pain evaluating test.

Table 3 shows shape variables of each test piece, and Table 4 shows an inferred value as the degree of pain in each test piece measured by the pain inferring device 10 after learning and a normalized value of the degree of pain in each test piece evaluated by the organoleptic test (organoleptic value). Here, the normalization was performed such that the maximum value and the minimum value before normalization are set at 1 and 0 respectively.

TABLE 3

| Test piece no. | 1-10 | 1-11 | 1-12 | 1-13 | 1-14 | 1-15 | 1-16 |
|---|---|---|---|---|---|---|---|
| H | 1.5 | 1.5 | 1.5 | 1.5 | 1.5 | 0.5 | 0.5 |
| B | 1.5 | 2.0 | 2.0 | 1.0 | 1.0 | 1.0 | 1.0 |
| R | 0.0 | 0.0 | 0.5 | 0.5 | 0.5 | 0.0 | 0.5 |
| S | 0.5 | 0.5 | 0.5 | 0.5 | 1.5 | 1.5 | 1.5 |

(unit: mm)

TABLE 4

| Test piece no. | 1-10 | 1-11 | 1-12 | 1-13 | 1-14 | 1-15 | 1-16 |
|---|---|---|---|---|---|---|---|
| Degree of pain (organoleptic value) | 0.00 | 0.02 | 0.31 | 0.63 | 1.00 | 0.29 | 0.92 |
| Degree of pain (inferred value) | 0.01 | 0.00 | 0.34 | 0.69 | 1.00 | 0.43 | 0.89 |

Figure 4:
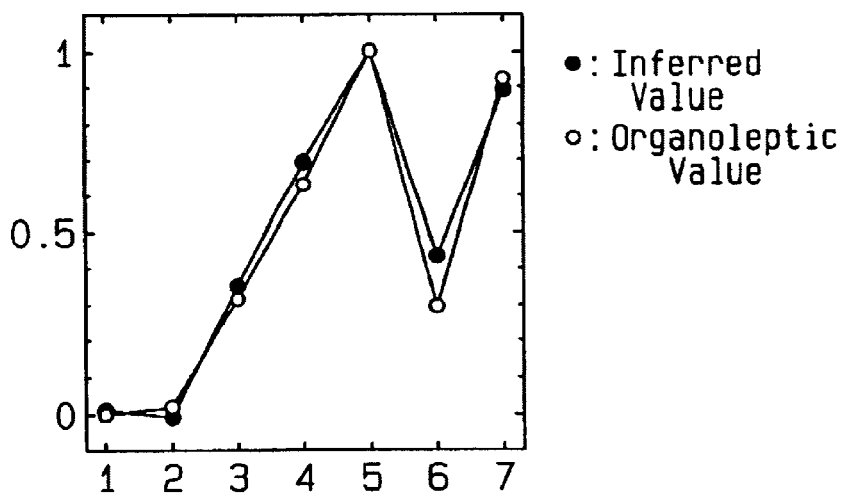
FIG. 4 is a graph showing the relationship between each test piece and the degree of pain in an inferred pain verification test.

FIG. 4 is a graph showing the relationship between each test piece and the degree of pain in the inferred pain verification test.

As is clear from FIG. 4, there was obtained a result that the inferred values as the degrees of pain measured by the pain inferring device 10 substantially coincide respectively with the organoleptic values obtained as the degree of pain in the organoleptic test.

(Second Embodiment)

Figure 5:
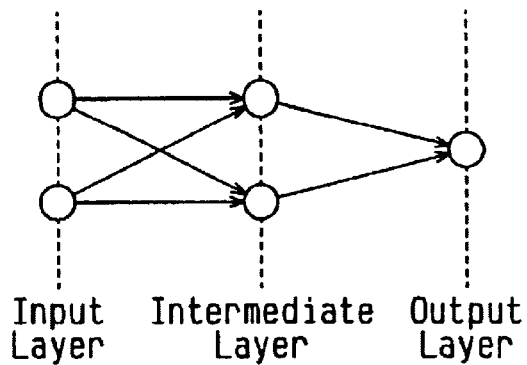
FIG. 5 is a schematic diagram of a neural network of the pain inferring device according to a second embodiment of the present invention.

Next, the pain inferring device according to a second embodiment of the present invention will be described referring to FIGS. 5 to 7.

The pain inferring device 10 of the second embodiment is provided with an input unit 11, an output unit 12, a main control unit 13, a learning storage unit 14 and a neural network 15. The neural network 15 in the second embodiment is of 2-input and 1-output system and includes an input layer, an intermediate layer and an output layer, as shown in FIG. 5. The intermediate layer has two elements (neurons).

Figure 6:
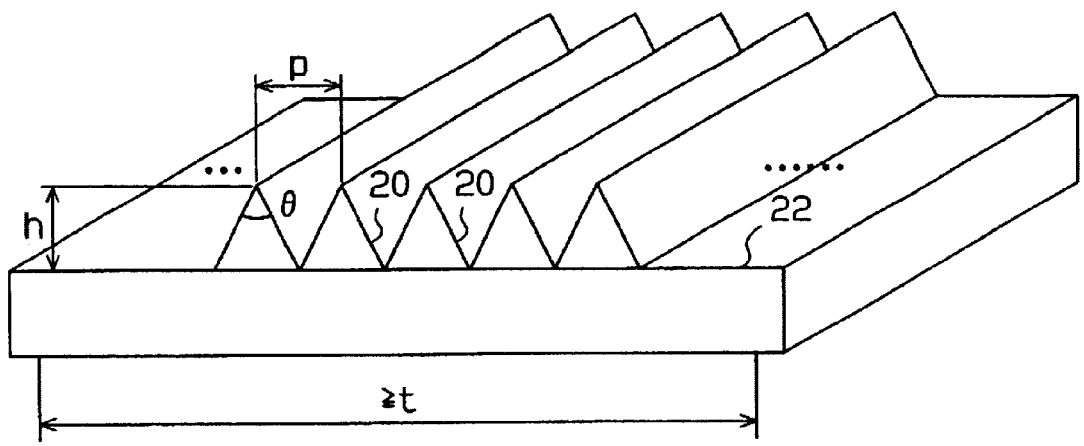
FIG. 6 is a schematic diagram of a test piece having a surface profile similar to that of a switch knob.

The pain inferring device 10 of the second embodiment is suitable for designing a switch knob (not shown) having a serrated surface, as shown in FIG. 6. In other words, a plurality of ribs 20 each having a triangular cross section are formed parallelwise on the surface of a test piece 22 in the second embodiment.

(Shape Data Setting)

Shape variables of the ribs 20 include the height h and the apex angle θ thereof. The shape variables are set based on the case where the ribs 20 are formed on a test piece 22 having a length t (30 mm, in this embodiment). Data of seven types of test pieces having ribs 20 with different shape variables are shown in Table 5.

TABLE 5

| Test piece no. | | 2-1 | 2-2 | 2-3 | 2-4 | 2-5 | 2-6 | 207 |
|---|---|---|---|---|---|---|---|---|
| Before normalization | h (mm) | 0.5 | 0.5 | 1.0 | 1.0 | 1.0 | 1.5 | 1.5 |
| | θ (deg) | 62 | 152 | 74 | 103 | 136 | 62 | 152 |
| After normalization | h | 0.05 | 0.05 | 0.50 | 0.50 | 0.50 | 0.95 | 0.95 |
| | θ | 0.05 | 0.05 | 0.17 | 0.46 | 0.50 | 0.05 | 0.95 |

(Pain Evaluating Test)

A pain evaluating test (organoleptic test) was performed using five adult male test subjects like in the first embodiment for seven test pieces 22. The results are shown in Table 6.

In the method of normalizing mean values in the second embodiment, the maximum theoretical value and the minimum theoretical value of the absolute evaluation point were determined according to the equation (1), and the approximate values 1 and 0 were set referring to the maximum theoretical value and the minimum theoretical value to perform normalization.

In the organoleptic test, seven test pieces are used as samples to be evaluated, so that there are obtained the maximum theoretical value 2.5 and the minimum theoretical value −2.5 according to the equation (1). However, if the above maximum theoretical value and the minimum theoretical values are used, the data are very likely to concentrate. Therefore, normalization was performed employing a maximum value of 1.5 and a minimum value of −1.5 therefor.

TABLE 6

| Test piece no. | 2-1 | 2-2 | 2-3 | 2-4 | 2-5 | 2-6 | 2-7 |
|---|---|---|---|---|---|---|---|
| Degree of pain before normalization | −1.37 | −0.49 | 0.26 | 0.77 | 0.37 | 0.89 | −0.43 |
| Degree of pain after normalization | 0.04 | 0.34 | 0.59 | 0.76 | 0.62 | 0.80 | 0.36 |

(Learning by Pain Inferring Device 10)

The shape variables (normalized values) shown in Table 5 as input values and the absolute evaluation point αi as an output value were inputted through the input unit 11 of the pain inferring device 10 to allow the neural network 15 to learn the relationship between the input and the output. The neural network 15 in the second embodiment learned according to the back-propagation algorithm. The input values and the output value were normalized such that they have the maximum value of 0.95 and the minimum value of 0.05, and the learning by the neural network 15 was terminated when the error of the output value reduced to a tolerable level of 0.01 or less. If shape variables of a certain serrated shape are inputted to the pain inferring device 10 after completion of learning, the device 10 infers the degree of pain to be given by the shape corresponding to the shape variables.

(Inferred Pain Verification Test)

After completion of learning, the inferred values as the degrees of pain measured by the pain inferring device 10 were compared with the degrees of pain reported by a plurality of (in this embodiment, five adult males) test subjects as a result of an organoleptic test (organoleptic values). In the verification test, there were prepared test pieces each having a shape according to shape variables which are different from those used in the pain evaluating test, to obtain organoleptic values as the degrees of pain to be given by the test piece evaluated by the organoleptic test and inferred values as the degrees of pain measured by the pain inferring device 10. The organoleptic values as the degrees of pain in the organoleptic test were calculated according to the equation (2).

Table 7 shows shape variables of each test piece before and after normalization respectively. Table 8 shows inferred values obtained as the degrees of pain given by the respective test pieces and the organoleptic values obtained as the degrees of pain in the organoleptic test, after normalization. Here, the normalization of the variables in Table 7 were performed based on the maximum value 0.95 and the minimum value 0.5 set in the shape variables in Table 5. The normalization in Table 8 was performed such that the maximum values and the minimum values of the organoleptic values, as well as, the inferred values before normalization are set at 1 and 0, respectively.

TABLE 7

| Test piece no. | | 2-8 | 2-9 | 2-10 | 2-11 | 2-12 | 2-13 | 2-14 |
|---|---|---|---|---|---|---|---|---|
| Before normalization | h (mm) | 0.80 | 0.90 | 0.50 | 1.50 | 0.80 | 1.20 | 1.50 |
| | θ (deg) | 53.13 | 118.07 | 83.97 | 86.05 | 86.30 | 109.56 | 126.87 |
| After normalization | h | 0.32 | 0.41 | 0.05 | 0.95 | 0.32 | 0.68 | 0.95 |
| | θ | −0.04 | 0.61 | 0.27 | 0.29 | 0.29 | 0.53 | 0.70 |

TABLE 8

| Test piece no. | 2-8 | 2-9 | 2-10 | 2-11 | 2-12 | 2-13 | 2-14 |
|---|---|---|---|---|---|---|---|
| Degree of pain (organoleptic value) | 0.00 | 0.85 | 0.05 | 1.00 | 0.59 | 0.94 | 0.89 |
| Degree of pain (inferred value) | 0.02 | 0.85 | 0.00 | 0.99 | 0.49 | 1.00 | 0.81 |

Figure 7:
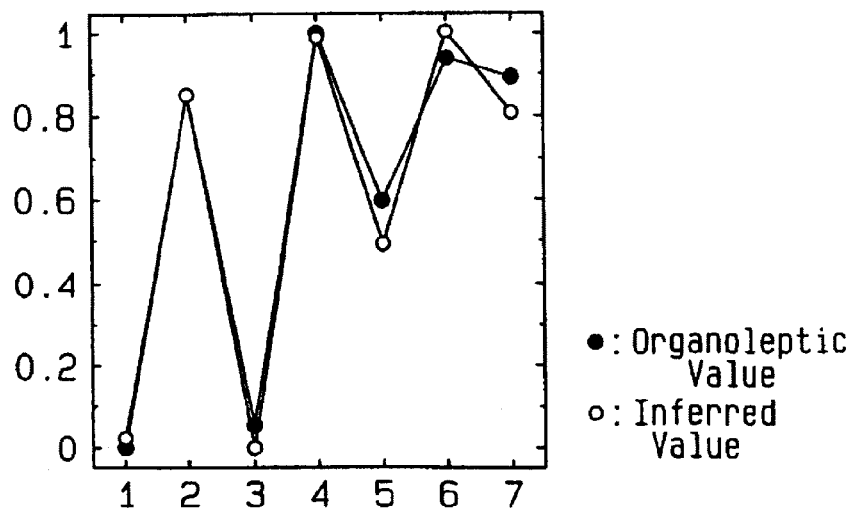
FIG. 7 is a graph showing the relationship between each test piece and the degree of pain in an inferred pain verification test.

FIG. 7 is a graph showing test piece nos. and the degrees of pain in the inferred pain verification test.

As is clear from FIG. 7, there was obtained a result that the inferred values as the degrees of pain measured by the pain inferring device 10 substantially coincide with the organoleptic values obtained as the degree of pain in the organoleptic test.

The pain inferring device 10 according to the present invention enjoys the following advantages:

(1) The pain inferring device 10 includes the input unit 11 for inputting shape variables (shape data) for specifying a shape, the neural network 15 learning the relationship between the input of the shape data and the output of the degree of pain to be given by a shape corresponding to the shape data to produce an input-output function indicative of the relationship between the input and the output, and the learning storage unit 14 for storing the input-output function. If shape variables are inputted through the input unit 11, the main control unit 13 supplies to the output unit 12, a degree of pain obtained from the neural network 15 based on the shape variables and the function. Thus, by inputting various kinds of shape variables to the pain inferring device 10, the degree of pain associated with the shape variables can easily be inferred by the device 10 at the stage of designing. In other words, once the pain inferring device 10 learns degrees of pain, there is no need of preparing a test piece having a new shape for measuring the degree of pain thereof.

(2) Learning by the neural network 15 easily enables inferring of the degree of pain; and (3) The neural network 15 produces an input-output function indicative of the relationship between known shape variables (shape data) as input values and the data on the degree of pain associated with the shape variables, as an output value, and if new shape variables are inputted to the pain inferring device 10, the device 10 infers the degree of pain based on the input-output function. According to this inferring method, the degree of pain can easily be inferred.

It should be apparent to those skilled in the art that the present invention may be embodied in many other specific forms without departing from the spirit or scope of the invention. Particularly, the present invention may be embodied in the following forms The hierarchical neural network 15 may be replaced with an interconnecting neural network.

The hierarchical neural network 15 may have two or more intermediate layers.

The surface profile of the test piece is not to be limited to the ribs 20, but the ribs 20 may be replaced, for example, with steps or protrusions. The protrusion may each have, for example, a truncated quadrangular pyramidal shape, a truncated conical shape or a hemispherical shape.

What is claimed is:

1. A pain inferring method, comprising the steps of:
    learning a relationship between shape date as an input and a degree of pain, as an output, felt by a person when he or she touches a shape corresponding to the shape data;
    producing an input-output function indicative of the relationship between the input and the output; and
    inferring, based on an input of new shape data, a degree of pain according to the input-output function.

2. The pain inferring method according to claim 1, wherein the learning step and the inferring step are performed using a neural network.

3. The pain inferring method according to claim 2, wherein the learning step includes learning the relationship between the input and the output in accordance with a back-propagation algorithm using the neural network.

4. The pain inferring method according to claim 3, further comprising the steps of:
    inputting predetermined shape data and a predetermined degree of pain; and
    terminating learning by the neural network, when an error between a degree of pain formed newly and the predetermined degree of pain reduces to a predetermined level or lower in the back-propagation algorithm.

* * * * *